US00PP26565P2

(12) United States Plant Patent
Zetterlund

(10) Patent No.: US PP26,565 P2
(45) Date of Patent: Mar. 29, 2016

(54) ***DICENTRA* PLANT NAMED 'LOVE HEARTS'**

(50) Latin Name: ***Dicentra peregrina*×*Dicentra oregana***
Varietal Denomination: Love Hearts

(71) Applicant: Henrik Zetterlund, Gotenborg (SE)

(72) Inventor: Henrik Zetterlund, Gotenborg (SE)

(73) Assignee: Compass Plants B.V., Hillegom (NL)

( * ) Notice: Subject to any disclaimer, the term of this patent is extended or adjusted under 35 U.S.C. 154(b) by 236 days.

(21) Appl. No.: 13/998,906

(22) Filed: Dec. 19, 2013

(51) Int. Cl.
*A01H 5/02* (2006.01)

(52) U.S. Cl.
USPC ..... Plt./426

(58) Field of Classification Search
USPC ..... Plt./426, 263.1
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Dicentra* plant named 'Love Hearts', characterized by its upright to outwardly spreading plant habit; freely flowering habit; light yellow green to white-colored flowers with purple to greyed red-colored apices; and good garden performance.

3 Drawing Sheets

Botanical designation: *Dicentra peregrina*×*Dicentra oregana.*

Cultivar denomination: 'LOVE HEARTS'.

BACKGROUND OF THE INVENTION

The present invention relates to a new and distinct *Dicentra* plant, botanically known as *Dicentra peregrina*×*Dicentra oregana* and hereinafter referred to by the name 'Love Hearts'.

The new *Dicentra* plant originated from a cross-pollination conducted by the Inventor in 2002 in Götenborg, Sweden, of an unnamed selection of *Dicentra peregrina*, not patented, as the female, or seed, parent with an unnamed selection of *Dicentra oregana*, not patented, as the male, or pollen, parent. The new *Dicentra* plant was discovered and selected by the Inventor as a single flowering plant within the progeny of the stated cross-pollination in a controlled environment in Götenborg, Sweden in June, 2004.

Asexual reproduction of the new *Dicentra* plant by cuttings in a controlled greenhouse environment in Heerhugowaard, The Netherlands since 2011 has shown that the unique features of this new *Dicentra* plant are stable and reproduced true to type in successive generations.

SUMMARY OF THE INVENTION

Plants of the new *Dicentra* have not been observed under all possible combinations of environmental conditions and cultural practices. The phenotype may vary somewhat with variations in environment conditions such as temperature and light intensity without, however, any variance in genotype.

The following traits have been repeatedly observed and are determined to be the unique characteristics of 'Love Hearts'. These characteristics in combination distinguish 'Love Hearts' as a new and distinct *Dicentra* plant:

1. Upright to outwardly spreading plant habit.
2. Freely flowering habit.

3. Light yellow green to white-colored flowers with purple to greyed red-colored apices.
4. Good garden performance.

Plants of the new *Dicentra* differ from plants of the female parent selection in the following characteristics:

1. Plants of the new *Dicentra* are larger and more vigorous than plants of the female parent selection.
2. Plants of the new *Dicentra* and the female parent selection differ in flower color as plants of the female parent selection have pinkish red-colored flowers.

Plants of the new *Dicentra* differ from plants of the male parent selection primarily in flower color as plants of the male parent selection have yellow-colored flowers.

Plants of the new *Dicentra* can also be compared to plants of *Dicentra peregrina*×*Dicentra eximia* 'Ivory Hearts', disclosed in U.S. Plant Pat. No. 15,599. Plants of the new *Dicentra* and 'Ivory Hearts' differ in the following characteristics:

1. Plants of the new *Dicentra* are shorter than plants of 'Ivory Hearts'.
2. Plants of the new *Dicentra* have darker-colored leaves than plants of 'Ivory Hearts'.
3. Peduncles of plants of the new *Dicentra* are more upright than peduncles of plants of 'Ivory Hearts'.
4. Plants of the new *Dicentra* and 'Ivory Hearts' differ in flower color as plants of 'Ivory Hearts' have creamy white-colored flowers.

BRIEF DESCRIPTION OF THE PHOTOGRAPHS

The accompanying colored photographs illustrate the overall appearance of the new *Dicentra* plant showing the colors as true as it is reasonably possible to obtain in colored reproductions of this type. Colors in the photographs may differ slightly from the color values cited in the detailed botanical description which accurately describe the colors of the new *Dicentra* plant.

The photograph on the first sheet comprises a side perspective view of a typical flowering plant of 'Love Hearts' grown in a container.

The photograph on the second sheet is a close-up view of typical leaves of 'Love Hearts'.

The photograph on the third sheet is a close-up view of typical flowers of 'Love Hearts'.

DETAILED BOTANICAL DESCRIPTION

The aforementioned photographs and following observations, measurements and values describe plants grown during the late summer in an outdoor nursery in Afferden, The Netherlands and under cultural practices typical of commercial *Dicentra* plant production. During the production of the plants, day temperatures ranged from 18° C. to 32° C. and night temperatures ranged from 6° C. to 20° C. Plants were one year old when the photographs and description were taken. In the following description, color references are made to The Royal Horticultural Society Colour Chart, 2007 Edition, except where general terms of ordinary dictionary significance are used.

Botanical classification: *Dicentra peregrina*×*Dicentra oregana* 'Love Hearts'.

Parentage:

*Female, or seed, parent.*—Unnamed selection of *Dicentra peregrina*, not patented.

*Male, or pollen, parent.*—Unnamed selection of *Dicentra oregana*, not patented.

Propagation:

*Type.*—By cuttings.

*Time to initiate roots plant, summer.*—About three weeks at temperatures about 20° C.

*Time to produce a rooted plant, summer.*—About six weeks at temperatures about 20° C.

*Root description.*—Thick, fleshy; white in color.

*Rooting habit.*—Freely branching; dense.

Plant description:

*Plant and growth habit.*—Herbaceous perennial grown as a container or garden plant; upright to outwardly spreading plant habit; leaves and flowering shoots developing from a basal rosette; low vigor to moderately vigorous growth habit.

*Plant height.*—About 22.9 cm.

*Plant width* (*spread*).—About 24.6 cm.

*Leaf description.*—Arrangement: Developing from a basal rosette; compound with three leaflets per leaf. Leaf length: About 8 cm. Leaf width: About 7.5 cm. Terminal leaflet length: About 4.3 cm. Terminal leaflet width: About 4.5 cm. Lateral leaflet length: About 4.6 cm. Lateral leaflet width: About 3.7 cm. Leaflet shape: Broadly ovate to nearly deltoid. Leaflet apex: Acute. Leaflet base: Short attenuate. Margin: Deeply incised to laciniate. Texture, upper and lower surfaces: Smooth, glabrous. Venation pattern: Pinnate. Color: Developing leaflets, upper surface: Close to N138B. Developing leaflets, lower surface: Close to 191B. Fully expanded leaflets, upper surface: Close to 189A to 189B; venation, close to 189A to 189B. Fully expanded leaflets, lower surface: Close to 191B; venation, close to 146B to 146C. Petioles: Length, from base of petiole to base of lateral leaflets: About 4.9 cm. Length, from base of lateral leaflets to base of terminal leaflet: About 2.5 cm. Diameter: About 2.5 mm by 2 mm. Texture, upper and lower surfaces: Smooth, glabrous. Color, upper surface: Close to 189A; towards the base tinged with close to N187C. Color, lower surface: Close to 183C to 183D tinged with close to 189A.

Flower description:

*Flower type and flowering habit.*—Single flattened cordate to saccate-shaped flowers arranged in loose compound panicles; inflorescences arising from the central crown; nodding flowers held above the foliar plane on strong peduncles; freely flowering habit with about nine open flowers per inflorescence and about 180 flowers developing per plant.

*Fragrance.*—None detected.

*Natural flowering season.*—Flowering occurs from May to July until first frost in The Netherlands.

*Postproduction longevity.*—Flowers maintain good substance and color for about ten days on the plant; flowers not persistent.

*Flower buds.*—Height: About 1.6 cm. Diameter: About 9 mm. Shape: Ovate. Color: Close to 150D; towards the apex, close to 150A to 150B with stripes, close to N77B; base tinged with close to 182C.

*Inflorescence height.*—About 6.2 cm.

*Inflorescence diameter.*—About 6.7 cm.

*Flower diameter, at widest point.*—About 1.7 cm.

*Flower diameter, at narrowest point.*—About 9 mm.

*Flower depth.*—About 1.9 cm.

*Petals.*—Quantity per flower: Typically four; two outer saccate petals fused in to a cordate structure and two inner petals fused at the apices. Length, outer petals: About 1.7 cm. Length, inner petals: About 8 mm. Width, outer petals: About 7 mm. Width, inner petals: About 3 mm. Shape, outer petals: Ovate. Shape, inner petals: Ovate. Apex, outer and inner petals: Rounded. Margin, outer and inner petals: Entire. Texture, upper and lower surfaces: Smooth, glabrous. Color, outer petals: Developing and fully expanded petals, outer surface: Close to 154D; towards the base, close to 155A flushed with close to 182D; with development, color becoming closer to 155C heavily flushed with close to 182D. Developing and fully expanded petals, inner surface: Close to 154D; towards the base, close to 155A flushed with close to 182D. Color, inner petals: Developing and fully expanded petals, outer surface: Close to 155A; upper half, close to N77B and 150C; with development, color becoming closer to 155C with upper half, close to N77D. Developing and fully expanded petals, inner surface: Close to 155A; upper half, close to 150C.

*Sepals.*—Quantity per flower: Typically two; opposite, closely appressed to base of corolla. Length: About 4.5 mm. Width: About 4 mm. Shape: Broadly ovate. Apex: Acute. Base: Cuneate. Margin: Entire. Texture, upper and lower surfaces: Smooth, glabrous. Color: Immature, upper and lower surfaces: Close to 151A slightly tinged with close to 184D. Mature, upper and lower surfaces: Close to 151B to 151C slightly tinged with close to 184C.

*Peduncles.*—Length: About 17.7 cm. Diameter: About 3 mm. Angle: Varying from upright to about 50° from vertical. Strength: Moderately strong. Texture: Smooth, waxy. Color: Close to 146A tinged with close to 187A; waxy layer, close to N187C to N187D.

*Pedicels.*—Length: About 1.3 cm. Diameter: About 1 mm. Angle: About 45° from vertical. Strength: Moderately strong. Texture: Smooth, glabrous. Color: Close to 138A to 138B.

*Reproductive organs.*—Stamens: Quantity per flower: Typically six. Filament length: About 1.3 cm. Filament color: Close to NN155C. Anther shape: Oblong. Anther length: About 1 mm. Anther color: Close to 22A. Pollen amount: Scarce. Pollen color: Close to 15A. Pistils: Quantity per flower: One. Pistil length: About 1 cm. Stigma color: Close to 154D. Style length: About 9 mm. Style color: Close to 145A to 145B. Ovary color: Close to 146B to 146C.

*Seeds.*—Quantity per fruit: About 20. Size: About 2.5 mm by 1.5 mm. Color: Close to 203A.

*Fruit.*—Size: About 16 mm by 7 mm. Color: Between N199A and N200B.

Disease & pest resistance: Plants of the new *Dicentra* have been not been observed to be resistant to pathogens and pests common to *Dicentra* plants.

Garden performance: Plants of the new *Dicentra* have been observed to have good garden performance and tolerate rain, wind and temperatures ranging from about −20° C. to about 40° C.

It is claimed:

1. A new and distinct *Dicentra* plant named 'Love Hearts' as illustrated and described.

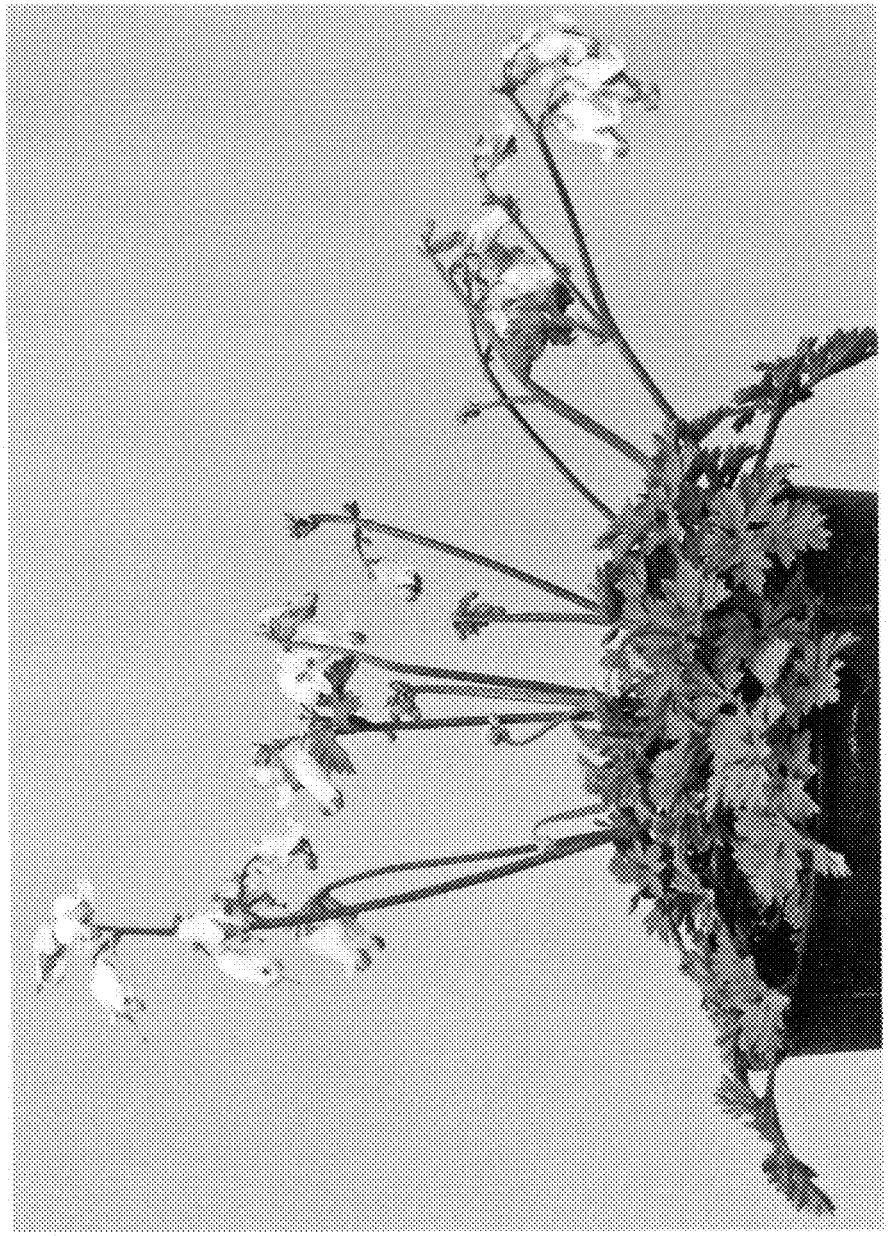

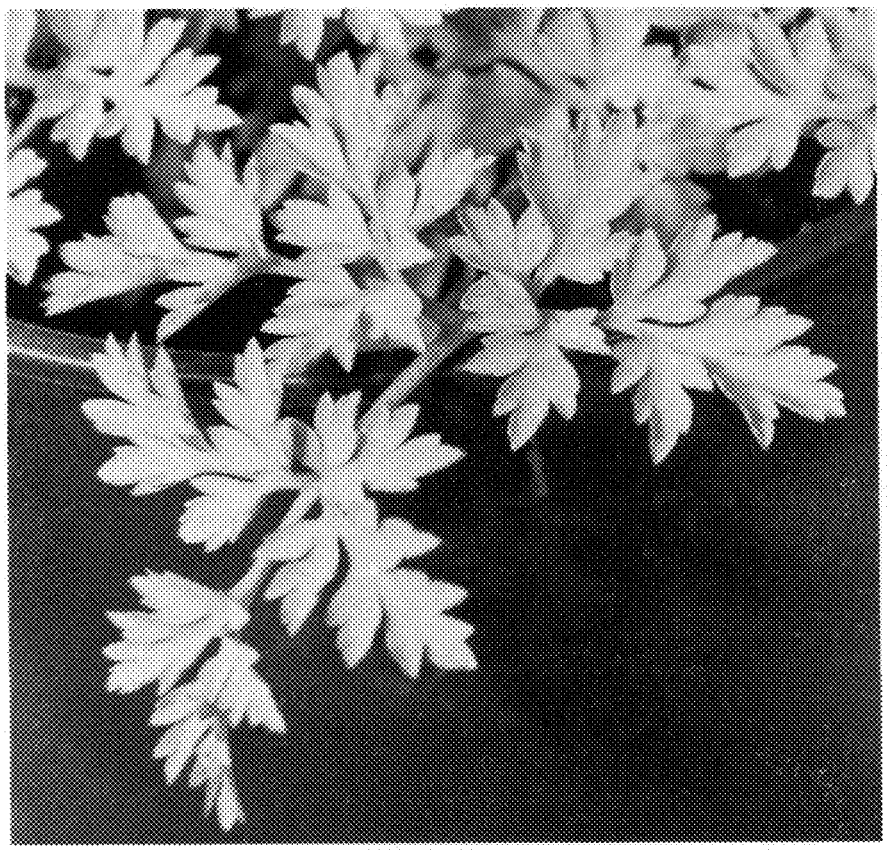

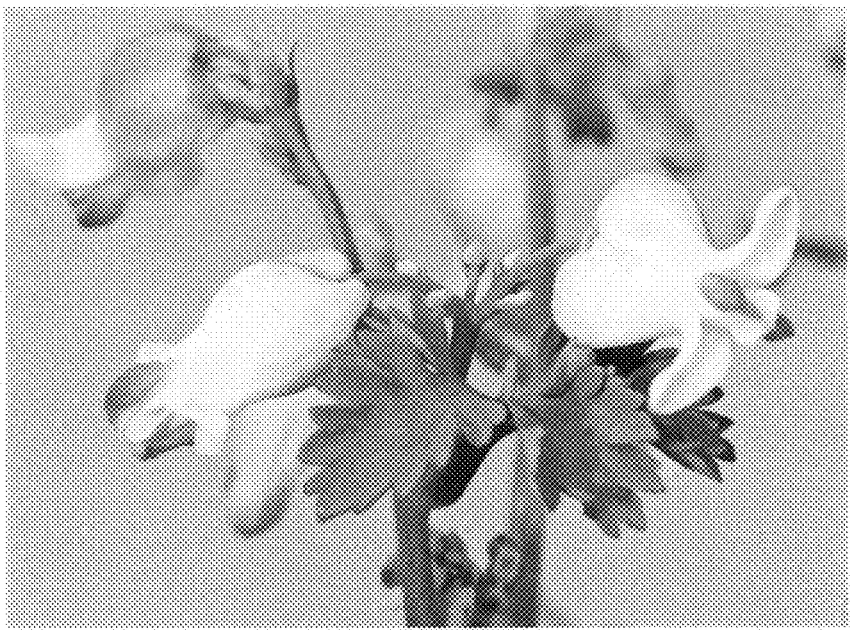

* * * * *